United States Patent [19]

Piekarsky

[11] Patent Number: 4,533,320
[45] Date of Patent: Aug. 6, 1985

[54] STABILIZING RETAINER SYSTEM

[76] Inventor: Jack Piekarsky, 23 Pilgrim Way, Wayne, N.J. 07470

[21] Appl. No.: 634,455

[22] Filed: Jul. 26, 1984

[51] Int. Cl.³ ............................................... A61C 3/00
[52] U.S. Cl. .......................................... 433/9; 433/10
[58] Field of Search .................. 433/9, 20, 10, 215; 128/89 A

[56] References Cited

U.S. PATENT DOCUMENTS

| | | | |
|---|---|---|---|
| Re. 30,332 | 7/1980 | Wallshein | 433/20 |
| 1,014,028 | 1/1912 | Angle | 433/10 |
| 3,250,003 | 5/1966 | Collito | 433/9 |
| 3,345,745 | 10/1967 | Muller | 433/9 |
| 3,949,478 | 4/1976 | Schinhammer | 433/3 |
| 4,015,334 | 4/1977 | Moss | 433/17 |
| 4,384,854 | 5/1983 | Garfinkel | 433/215 |
| 4,386,908 | 6/1983 | Kurz | 433/9 |
| 4,433,960 | 2/1984 | Garito et al. | 433/215 |

OTHER PUBLICATIONS

"Biting Back"; Comer, Nancy; New York Times, 1-1-3-85, p. 11.

*Primary Examiner*—Hugh R. Chamblee
*Assistant Examiner*—K. McNamara
*Attorney, Agent, or Firm*—Samuelson & Jacob

[57] ABSTRACT

A system for maintaining the position of a series of teeth in the mouth includes a thin, conformable wire spanning the series of teeth and secured to the surfaces of the teeth by a plurality of individual bonding pads placed over the conformable wire and bonded one each to each tooth to secure the conformable wire in place and to stabilize the position of the series of teeth.

16 Claims, 12 Drawing Figures

STABILIZING RETAINER SYSTEM

The present invention relates generally to a system for the retention of teeth in a desired position in the mouth and pertains, more specifically, to apparatus and method for effectively retaining and maintaining the position of a series of upper or lower teeth within the mouth.

It is well known in orthodontics to retain and maintain natural teeth in a desired position in the mouth through the use of stabilizing retainers. Whenever it becomes necessary to immobilize teeth which have been moved, as by the use of an orthodontic appliance, or by dislocation as a result of periodontal disease, the teeth are stabilized by utilizing various available retainer systems. Both lingual and labial retaining devices have been in use for quite some time, and more recent innovations have employed a variety of structural elements bonded to the surfaces of teeth to be stabilized. In order to be fitted properly, currently available retaining devices require either customized fabrication outside the practitioner's office, or extensive fitting work by the practitioner directly on the patient.

It is an object of the present invention to provide a stabilizing retainer system which is fitted to a patient directly, with relative ease, so as to enable a practitioner effectively to immobilize teeth and establish appropriate positioning of the teeth in an expeditious manner within the practitioner's own office.

Another object of the invention is to provide a stabilizing retainer system which is highly versatile, enabling its use in treating a variety of conditions, in an economical manner.

Still another object of the invention is to provide a stabilizing retainer system which is less bulky and therefore less obtrusive when in place and in which the components of the system interfere less with the normal function and maintenance of the teeth in connection with which the system is used.

Yet another object of the invention is to provide a stabilizing retainer system which is less likely to irritate or injure tissue in the vicinity of the installed components of the system.

A further object of the invention is to provide a stabilizing retainer system which is easy to maintain after it is in place within the mouth of a patient.

A still further object of the invention is to provide a stabilizing retainer system which is economical to manufacture and to use, enabling effective employment of the system at minimal cost.

The above objects, as well as still further objects and advantages, are attained by the present invention, which may be described briefly as a stabilizing retainer for maintaining the position of a series of teeth in the mouth, each tooth of the series including a surface area bounded by peripheral edges and having given surface contours, the stabilizing retainer comprising: a relatively thin, conformable wire for placement in a predetermined position wherein the wire spans the series of teeth and is conformed into contiguity with the series of teeth; a plurality of individual, relatively thin bonding pads for being bonded, one each to each tooth of the series of teeth, each bonding pad including peripheral edges, an obverse surface and a reverse surface; basal surface portions on the reverse surface of each bonding pad, the basal surface portions having a surface contour complementary to the surface area of a corresponding tooth of the series of teeth and a surface area less than the corresponding surface area of the tooth such that the peripheral edges of each bonding pad will be spaced from the peripheral edges of the corresponding tooth when the bonding pad is bonded to that tooth; and a transverse channel in each bonding pad, the transverse channel being generally complementary to the wire and open toward the reverse surface for receiving the conformable wire to locate each bonding pad and secure the conformable wire in the predetermined position when the bonding pads are placed over the conformable wire and bonded to the series of teeth.

The invention will be understood more fully, while still further objects and advantages will become apparent, in the following detailed description of a preferred embodiment thereof, illustrated in the accompanying drawing, in which.

Figure 1:
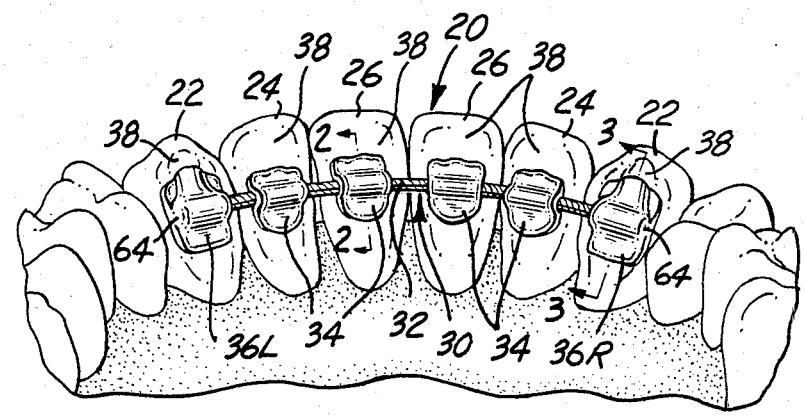
FIG. 1 is a pictorial view of the lingual surfaces of a series of anterior teeth showing a stabilizing retainer system of the present invention installed thereon.

Referring now to the drawing, and especially to FIG. 1 thereof, a series of anterior teeth 20 are depicted pictorially and are seen to include canines 22, lateral incisors 24 and central incisors 26. A stabilizing retainer constructed and installed in accordance with the invention is shown generally at 30 and is seen to include a lingual wire 32 and a plurality of bonding pads 34 and 36 secured to the lingual surfaces 38 of anterior teeth 20.

Figure 2:
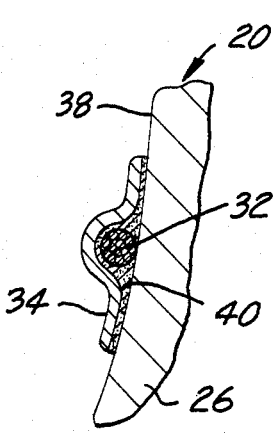
FIG. 2 is an enlarged cross-sectional view taken along line 2—2 of FIG. 1, showing an incisor pad of the system affixed to a tooth.
Figure 3:
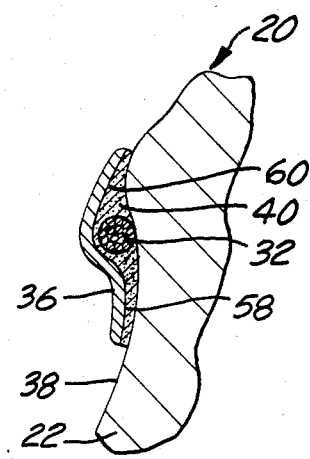
FIG. 3 is an enlarged cross-sectional view taken along line 3—3 of FIG. 1, showing a canine pad of the system affixed to another tooth.

A best seen in FIGS. 2 and 3, as well as in FIG. 1, bonding pads 34 and 36 are secured to lingual surfaces 38 of anterior teeth 20 by means of an orthodontic bonding material shown in the form of adhesive layer 40. Adhesive layer 40 also anchors lingual wire 32 relative to bonding pads 34 and 36 so that anterior teeth 20 all are fixed relative to one another and are held in position by lingual wire 32.

Figure 4:
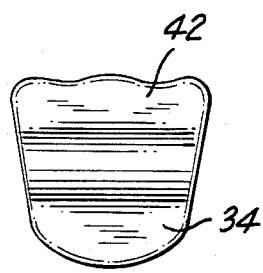
FIG. 4 is a plan view of the incisor pad illustrated in FIG. 2.
Figure 5:
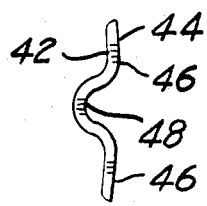
FIG. 5 is an end elevational view of the pad of FIG. 4.

Turning now to FIGS. 4 and 5, bonding pads 34 are incisor pads and are provided with a configuration best suited to complement the contours of lingual surfaces 38 of lateral incisors 34 and central incisors 26. The obverse surfaces 42 of bonding pads 34 are provided with smooth contours while the reverse surfaces 44 include basal portions 46 which preferably are roughened somewhat for enhancing adherence to the adhesive layer 40. Basal portions 46 are somewhat convex to complement the concave contour of the lingual surfaces 38 of the incisors 24 and 26. A channel 48 extends transversly across each bonding pad 34 and is open toward the basal portions 46 to receive lingual wire 32. Channel 48 has dimensions corresponding to the diameter of lingual wire 32 in order to enable positive location of bonding pad 34 in proper position relative to lingual wire 32 and the corresponding tooth surfaces as will be explained hereinafter.

Figure 6:
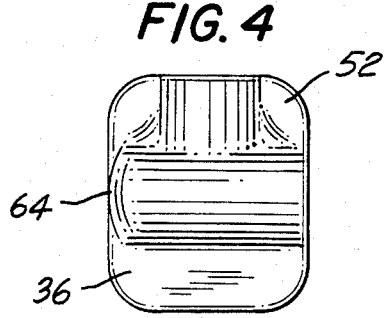
FIG. 6 is a plan view of the canine pad illustrated in FIG. 3.
Figure 7:
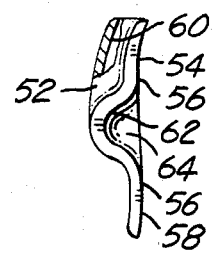
FIG. 7 is an end elevational view of the pad of FIG. 6.

As seen in FIGS. 6 and 7, bonding pads 36, which are canine pads, are provided with a configuration best suited to complement the contours of lingual surfaces 38 of canines 22. The obverse surfaces 52 of bonding pads 36 are provided with smooth contours while the reverse surfaces 54 include basal portions 56 which preferably are roughened somewhat for enhancing adherence to the adhesive layer 40. Basal portions 56 are somewhat convex along areas 58 and are concave along further areas 60 (also see FIG. 3) to complement the concave and convex contours of the corresponding areas of lingual surfaces 38 of the canines 22. A channel 62 extends transversely across each bonding pad 36 and is open toward the basal portions 56 to receive lingual wire 32. Channel 62 has dimensions corresponding to the diameter of lingual wire 32 in order to enable positive location of bonding pad 36, relative to lingual wire 32 and the corresponding tooth surfaces, as will be explained hereinafter.

Canine bonding pads 36 are provided in left-hand and right-hand configurations. Thus, the canine bonding pad 36 depicted in FIGS. 6 and 7 is a left-hand bonding pad and includes a left end wall 64 which closes the channel 62 at the left end of canine bonding pad 36. The left-hand canine bonding pad is designated as 36L in FIG. 1. In a right-hand canine bonding pad, designated at 36R in FIG. 1, end wall 64 is placed at the right end of the bonding pad, all for purposes which will be described below.

The procedure for installing stabilizing retainer 30 is described in connection with FIGS. 8 through 12. Prior to the installation, the teeth 20 to which bonding pads 34 and 36 are to be affixed are subjected to a thorough prophylaxis treatment, using a plain pumice, especially on the lingual surfaces 38. A measurement is made of the length of the arch from the mid-third of the left cuspid or canine 22 to the mid-third of the right cuspid or canine 22, as by bending a segment of brass wire (not shown) along the arch and cutting the brass wire to length. Using the measured length of brass wire as a gage, the lingual wire 32 is cut to the required length. Then, the lingual wire 32 is formed into the approximate shape of the patient's arch.

Figure 8:
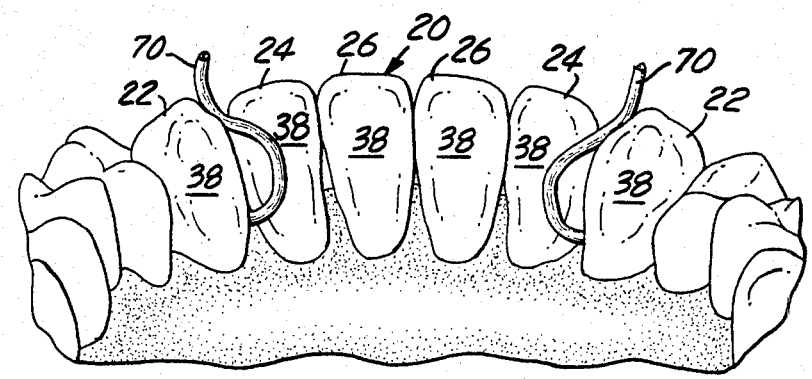
FIGS. 8 through 12 are pictorial views similar to FIG. 1 and illustrating the installation procedure of the present invention.
Figure 9:
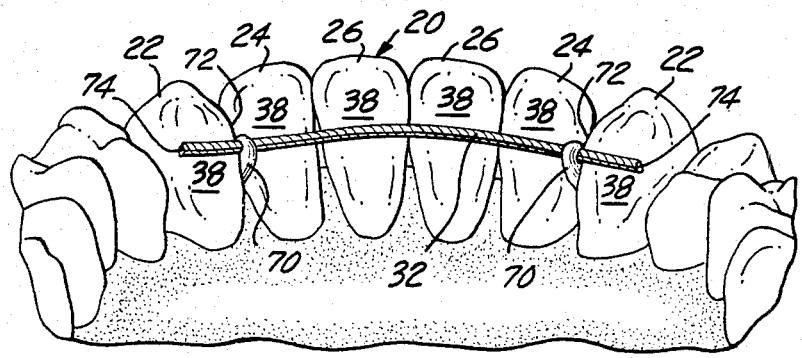

A length 70 of dental floss is placed between each canine 22 and the adjacent lateral incisor 24, as seen in FIG. 8. Using a plugger, lingual wire 32 is conformed to the contours of the lingual surfaces 38. The lengths 70 of dental floss then are looped over lingual wire 32 at each cuspid-lateral area 72 and the lengths 70 of dental floss are pulled forward to secure the lingual wire 32 in correct position against the lingual surfaces 38, as illustrated in FIG. 9.

Figure 10:
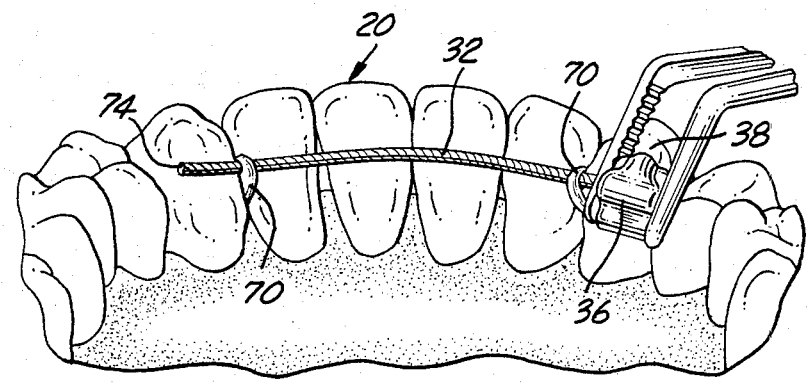
Figure 11:
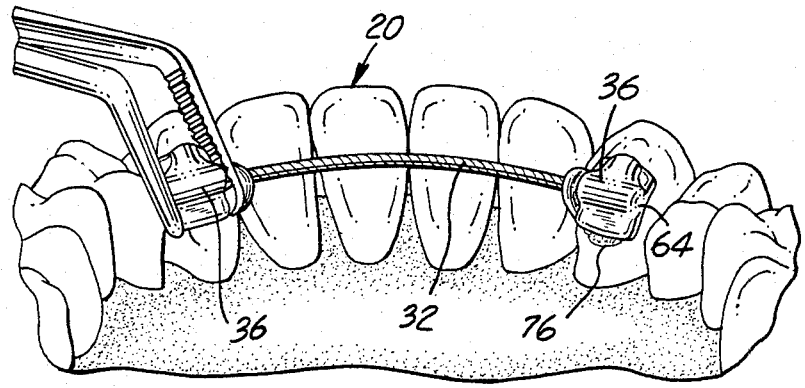

Each of the ends 74 of the lingual wire 32 is then anchored by affixing a canine bonding pad 36 in place over an end 74 of the lingual wire by adhering the bonding pads 36 to the lingual surfaces 38 of the canines 22, as shown in FIGS. 10 and 11. Prior to placing the bonding pads 36 as shown, the bonding pads are loaded with an appropriate orthodontic bonding material; that is, the reverse surfaces 54, including basal portions 56, are coated with bonding material and the channel 62 is filled with bonding material. The complementary contours of the basal portions 56 and corresponding areas of the lingual surfaces 38 will assure proper adherence between the bonding pads 36 and canines 22. The fitting of the channel 62 over the properly located lingual wire 32 will locate each bonding pad 36 positively in proper position relative to lingual wire 32 and lingual surfaces 38 of the tooth, enabling such location to be accomplished with relative ease.

It is noted that end walls 64 of the bonding pads 36 close off the ends 74 of the lingual wire 32 to preclude any relative movement between the lingual wire 32 transversely and bonding pads 36 and establish a relatively rigid connection between lingual wire 32 and bonding pads 36. In addition, the end walls 64 provide a smooth, capped end configuration at the terminal ends of the retainer 30, with the bonding pads 36 serving as end pads.

Figure 12:
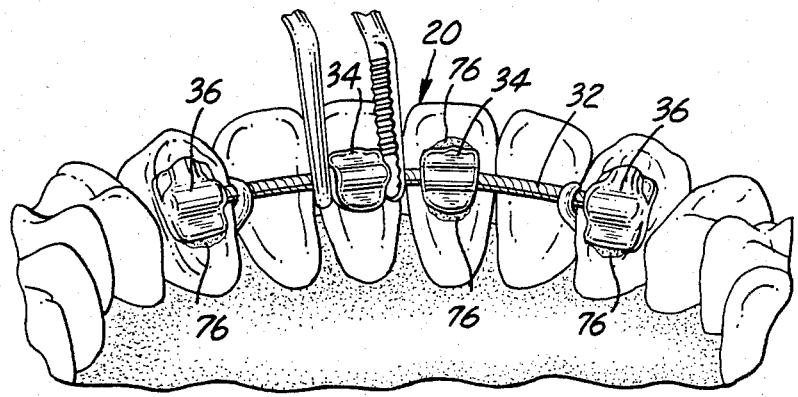

Next, incisor bonding pads 34 are affixed to central incisors 26, as illustrated in FIG. 12, over lingual wire 32, to secure lingual wire 32 to the lingual surfaces 38 of central incisors 26. Here again, the bonding pads 34 are loaded with bonding material prior to placement of the bonding pads 34 over the lingual wire 32 and against the lingual surfaces 38. The complementary contours of the basal portions 46 and the corresponding areas of the lingual surfaces 38 will assure proper adherence between the bonding pads 34 and the central incisors 26. The fitting of the channel 48 over the properly located lingual wire 32 will locate each bonding pad 34 positively in proper position relative to lingual wire 32 and lingual surfaces 38 of the tooth with relative ease. In a similar manner, further bonding pads 34 are affixed to the lateral incisors 24, over lingual wire 32, to secure lingual wire 32 to the lingual surfaces 38 of lateral incisors 24.

Any excess bonding material which appears as flash 76 at the peripheral edges of the bonding pads 34 and 36 is removed and the remaining bonding material is allowed to set. When the bonding material is fully set, the lengths 70 of dental floss are removed from the interproximal spaces at cuspid-lateral areas 72 and the installation is complete, as illustrated in FIG. 1.

The installation procedure is simple, quick and effective and can be accomplished readily in the practitioner's office. The ability to cut and fit lingual wire 32, then locate and hold lingual wire 32 in appropriate position and then secure lingual wire 32 in the appropriate position by positively locating and securing individual independent bonding pads 34 and 36 to teeth 20 enables the practitioner to fit stabilizing retainer 30 in the office, directly to a patient, without requiring extensive and time-consuming fabrication outside the office.

Lingual wire 32 preferably is constructed in the form of a multi-strand stainless steel wire which is strong in tension yet conformable so as to be easily conformed to the appropriate lingual contours and easily located relative to lingual surfaces 38 to assure proper location of the lingual wire 32 and subsequent positioning of the bonding pads relative to the teeth 20. The multi-stranded construction is tough enough to withstand abrasion and other conditions encountered during service, and can be of a very small diameter so as to remain unobtrusive. Lingual wires having a diameter as small as 0.026 inch have been used successfully.

The bonding pads 34 and 36 likewise are small in total area and preferably are die formed from thin stainless steel sheet. The area of each bonding pad is considerably smaller than the area of the lingual surface of the tooth to which the bonding pad will be attached so that the peripheral edges of the bonding pads will be spaced away from the corrresponding peripheral edges of the tooth. Thus, the bonding pads will not come into contact with gingival tissue and will not become an irritant to such tissue. Further, the spacing of the peripheral edges of the bonding pads away from the interproximal spaces reduces interference with flossing procedures and enables continued good dental hygiene. Additionally, the unobtrusive structure of stabilizing retainer 30 is aesthetically more desirable.

The bonding pads 34 and 36 are formed with the obverse surfaces following the contours of the reverse surfaces which, in turn, follow generally the contours of the lingual surfaces 38 of teeth 20 so as essentially to replicate those contours at the obverse surfaces. The relatively thin cross-section of bonding pads 34 and 36, preferably about 0.015 inch, coupled with the smooth tooth-matching contours of the obverse surfaces of the bonding pads renders the bonding pads unobtrusive, contributing to patient comfort and ease of maintaining proper oral hygiene while stabilizing retainer 30 is in use. Preferably, the peripheral edges of the bonding pads are smoothed to eliminate all rough edges. The elimination of rough edges and the absence of exposed bonding material further enhances patient comfort and ease of maintaining proper oral hygiene.

The employment of individual bonding pads in connection with a lingual wire enables ease of maintenance. Should it become necessary to adjust or replace a particular bonding pad, only that bonding pad need be removed and replaced without disturbing the remainder of the installation. Despite the relatively small dimensions of the bonding pads, the bonding pads are easily located for proper placement by engagement of the channel in each bonding pad with the anchored lingual wire.

The simplified construction of the component parts of stabilizing retainer 30 enables economical fabrication and low cost. Because of the low cost, it becomes practical for a practitioner to maintain in the office an inventory of component parts so that component parts always are on hand for direct application of a stabilizing retainer 30 to a patient, as required.

Although the illustrated embodiment is in the form of a lingual device, essentially the same construction may be employed in a labial device to attain similar advanges.

It is to be understood that the above detailed description of an embodiment of the invention is provided by way of example only. Various details of design and construction may be modified without departing from the true spirit and scope of the invention as set forth in the appended claims.

The embodiments of the invention in which an exclusive property or privilige is claimed are defined as follows:

1. A stabilizing retainer for maintaining the position of a series of teeth in the mouth, each tooth of the series including a surface area bounded by peripheral edges and having given surface contours, said stabilizing retainer comprising:

a relatively thin, conformable wire for placement in a predetermined position in which the wire spans the series of teeth and is conformed into contiguity with the series of teeth;

a plurality of individual, relatively thin bonding pads for being bonded, one each to each tooth of the series of teeth, each bonding pad including peripheral edges, an obverse surface and a reverse surface;

basal surface portions on the reverse surface of each bonding pad, the basal surface portions having a surface contour complementary to the surface area of a corresponding tooth of said series of teeth and a surface area less than the corresponding surface area of said tooth such that the peripheral edges of each bonding pad will be spaced from the peripheral edges of the corresponding tooth when said bonding pad is bonded to said tooth; and a transverse channel in each bonding pad, the transverse channel being generally complementary to the wire and open toward the reverse surface for receiving the conformable wire to locate each bonding pad and secure the conformable wire in said predetermined position when the bonding pads are placed over the conformable wire and bonded to said series of teeth.

2. The invention of claim 1 wherein at least portions of the obverse surface of each bonding pad have surface contours following the surface contours of opposite portions of the reverse surface of the bonding pad such that the obverse surfaces generally follow and essentially replicate the surface contours of the series of teeth to which the bonding pads are to be bonded.

3. The invention of claim 1 wherein the conformable wire includes a plurality of strands of metal wire.

4. The invention of claim 3 wherein at least portions of the obverse surface of each bonding pad have surface contours following the surface contours of opposite portions of the reverse surface of the bonding pad such that the obverse surfaces generally follow and essentially replicate the surface contours of the series of teeth to which the bonding pads are to be bonded.

5. The invention of claim 1 wherein the predetermined position is located along lingual surfaces of said series of teeth, said lingual surfaces including concave surface contours, and the basal surface portions of the bonding pads include convex surface contours of said lingual surfaces.

6. The invention of claim 5 wherein the conformable wire includes a plurality of strands of metal wire.

7. The invention of claim 5 wherein the obverse surface of each bonding pad includes concave surface contours generally follow the surface contours of opposite portions of the reverse surface of the bonding pad such that the obverse surfaces generally follow the surface contours of the lingual surfaces of said series of teeth so as essentially to replicate the surface contours of the lingual surfaces.

8. The invention of claim 7 wherein the conformable wire includes a plurality of strands of metal wire.

9. The invention of claim 1 wherein the conformable wire includes opposite ends and the bonding pads include end bonding pads for placement at the opposite ends of the conformable wire, said end bonding pads each having an end wall closing off the transverse channel adjacent the corresponding end of the conformable wire when the end bonding pads are placed over the conformable wire and bonded to the corresponding teeth.

10. The invention of claim 9 wherein at least portions of the obverse surface of each bonding pad have surface contours following the surface contours of opposite portions of the reverse surface of the bonding pad such that the obverse surfaces generally follow and essentially replicate the surface contours of the series of teeth to which the bonding pads are to be bonded.

11. The invention of claim 10 wherein the conformable wire includes a plurality of strands of metal wire.

12. The invention of claim 10 wherein the predetermined position is located along lingual surfaces of said series of teeth, said lingual surfaces including concave surface contours, and the basal surface portions of the bonding pads include convex surface contours of said lingual surfaces.

13. The method of stabilizing the position of a series of teeth in the mouth, each tooth of the series including a surface area bounded by peripheral edges and having given surface contours, said method comprising the steps of:

placing and conforming a relatively thin, conformable wire in a predetermined position wherein the wire spans the series of teeth and is conformed into contiguity with the series of teeth;

holding the conformable wire in said predetermined position;

placing a plurality of individual, relatively thin bonding pads over the conformable wire and against the series of teeth, with one bonding pad against each tooth of the series of teeth;

bonding each bonding pad to a corresponding tooth and to the conformable wire to secure the wire in said predetermined position and stabilize the position of the series of teeth.

14. The invention of claim 13 wherein the surface area of each bonding pad is less than the surface area of the tooth to which the bonding pad is to be bonded and wherein the step of placing each bonding pad against a corresponding tooth includes spacing the bonding pad away from the peripheral edges of the surface area of the tooth.

15. The invention of claim 13 wherein the predetermined position of the conformable wire is located along lingual surfaces of said series of teeth and the bonding pads are placed against the lingual surfaces of the teeth.

16. The invention of claim 15 wherein the surface area of each bonding pad is less than the surface area of the tooth to which the bonding pad is to be bonded and wherein the step of placing each bonding pad against a corresponding tooth includes spacing the bonding pad away from the peripheral edges of the surface area of the tooth.

* * * * *